United States Patent
Zhou

(10) Patent No.: US 8,513,029 B2
(45) Date of Patent: Aug. 20, 2013

(54) DISCRETE CONTACT MR BIO-SENSOR WITH MAGNETIC LABEL FIELD ALIGNMENT

(75) Inventor: Yuchen Zhou, Milpitas, CA (US)

(73) Assignee: Headway Technologies, Inc., Milpitas, CA (US)

(*) Notice: Subject to any disclaimer, the term of this patent is extended or adjusted under 35 U.S.C. 154(b) by 1439 days.

(21) Appl. No.: 11/900,370

(22) Filed: Sep. 11, 2007

(65) Prior Publication Data
US 2009/0065359 A1   Mar. 12, 2009

(51) Int. Cl.
*G01N 33/553*   (2006.01)
*G01N 33/53*   (2006.01)

(52) U.S. Cl.
USPC ............................................................ 436/518

(58) Field of Classification Search
USPC ............................................................ 435/518
See application file for complete search history.

(56) References Cited

U.S. PATENT DOCUMENTS

| | | | |
|---|---|---|---|
| 5,981,297 A | 11/1999 | Baselt | |
| 6,743,639 B1 | 6/2004 | Tondra et al. | |
| 6,875,621 B2 | 4/2005 | Tondra | |
| 7,172,904 B2 | 2/2007 | Engel et al. | |
| 7,179,383 B1 | 2/2007 | Porter et al. | |
| 2003/0132746 A1* | 7/2003 | Cox | 324/207.26 |
| 2007/0114180 A1 | 5/2007 | Ramanathan et al. | |
| 2007/0159175 A1 | 7/2007 | Prins | |

OTHER PUBLICATIONS

"A biosensor based on magnetoresistance technology", by David R. Baselt et al., Biosensors & Bioelectronics 13 (1998) 731-739, Elsevier, 0956-5663/98.
"The BARC biosensor applied to the detection of biological warfare agents", by R.L. Edelstein et al., Biosensors & Bioelectronics 14 (2000) 805-813), Elsevier, 0956-5663/00.
"A DNA array sensor utilizing magnetic microbeads and magnetoelectronic detection", by M.M. Miller et al., Jrnl. of Magnetism and Magnetic Materials 225 (2001) 138-144.
"Single magnetic microsphere placement and detection on-chip using current line designs with integrated spin valve sensors. Biotechnological applications" by D.L. Graham et al., Jrnl. of Appl. Physics, vol. 91, No. 10, May 15, 2002, pp. 7786-7788.
Biodetection using magnetically labeled biomeolcules and arrays of spin valve sensors (invited), by H.A. Ferreira et al., Jrnl. of Appl. Physics, vol. 93, No. 10, May 15, 2003, pp. 7281-7286.
"Detection of single micron-sized magnetic bead and magnetic nanoparticles using spin valve sensors for biological applications", by Guanxiong Li et al., Jrnl. of Appl. Physics, vol. 93, No. 10, May 15, 2003, pp. 7557-7559.

(Continued)

*Primary Examiner* — Mark Shibuya
*Assistant Examiner* — Pensee Do
(74) *Attorney, Agent, or Firm* — Saile Ackerman LLC; Stephen B. Ackerman

(57) ABSTRACT

The invention describes a family of sensors for assaying macro-molecules and/or biological cells in solution. Each sensor has the form of a well (a hollow cylinder having a floor but no lid) or a trench whose walls comprise a plurality of GMR or TMR devices. Suitably shaped magnets located below each well's floor pull labeled particles into the well/trench and up against the inner wall where a field gradient orients them for optimum detection. Any unattached labels that happen to also be in the well/trench are removed through suitably sized holes in the floor.

17 Claims, 8 Drawing Sheets

(56) References Cited

OTHER PUBLICATIONS

"Model and Experiment of Detecting Multiple Magnetic Nanoparticles as Biomolecular Labels by Spin Valve Sensors", by Guanxiong Li et al., IEEE Trans. on Magnetics, vol. 40, No. 4, Jul. 2004, pp. 3000-3002.

"Towards a magnetic microarray for sensitive diagnostics", by Shan X. Wang et al., Jrnl. of Magnetism and Magnetic Materials 293 (2005) 731-736 ,Elsevier 0304-8853.

"Effect of spin-valve sensor magnetostatic fields on nano-bead detection for biochip applications", by H.A. Ferreira et al., Jrnl. of Appl. Physics 97, 10Q904 (2005) pp. 1-3.

"Interaction of multiple iron balls in magentic fields", by M. Murakami et al., Jrnl. of Appl. Physics 97, 083911 (2005) pp. 1 to 3.

"In situ detection of single micron-sized magnetic beads using magnetic tunnel junction sensors", by Weifeng Shen et al., Appl. Physics Letters 86, 25390(2005) pp. 1-3.

Eneflux-Armtek Magnetics, Sintered Neodymium Standard Parts: Magnetic Disks , Rectangular Magnets and Ring Magnets, ISO / TS 16949:2002.

"New Single-Molecule Detector", by Prachi Patel-Predd, Tues. ,Jul. 10, 2007 ,Technology Review : pp. 1-4, found Aug. 13, 2007 on file://c:\Documents and Settings\Administrator\Application Data\Qualcomm\Eudora\attac . . . .

Physics of Ferromagnetism, Second Edition, by Soshin Chikazumi, English edition prepared with the assistance of C. D. Graham, Jr. Table 22.1, Oxford University Press, New York, (c) 1997.

\* cited by examiner

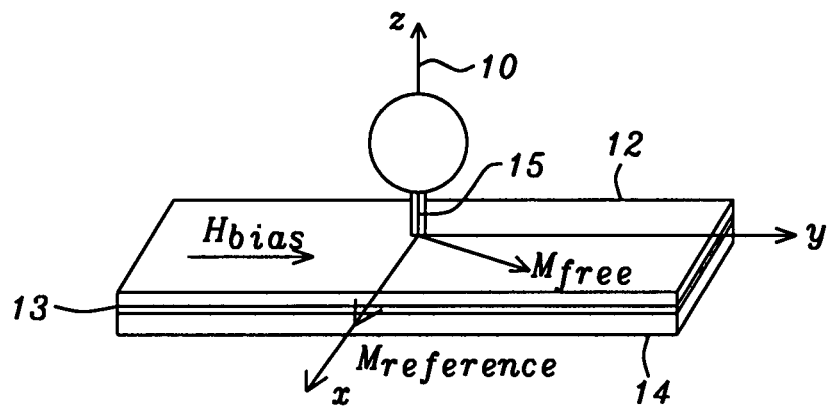
*FIG. 1 – Prior Art*
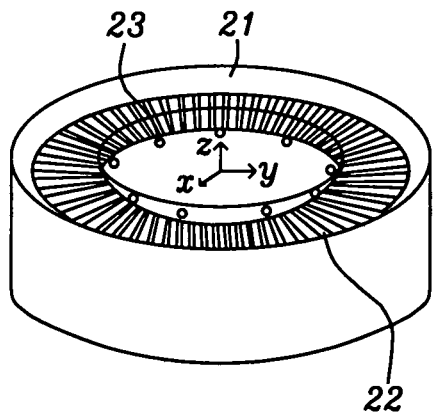
*FIG. 2a*
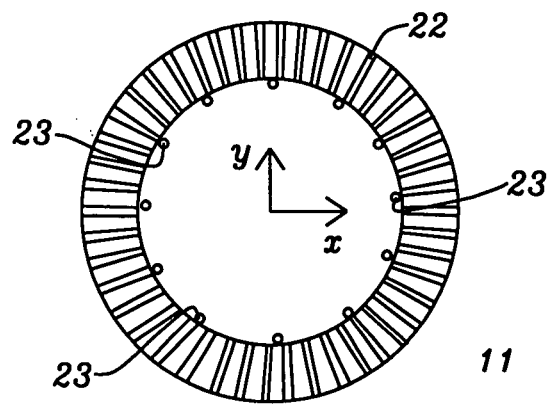
*FIG. 2b*

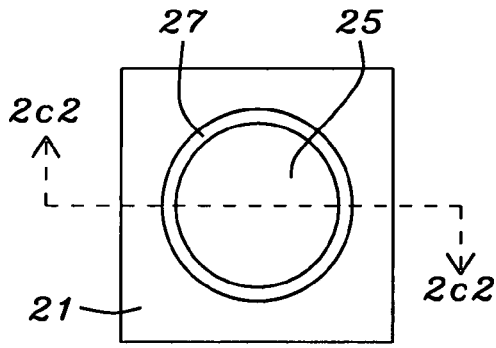
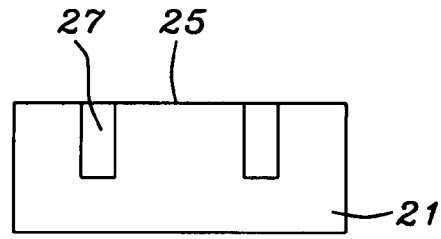
FIG. 2c1      FIG. 2c2
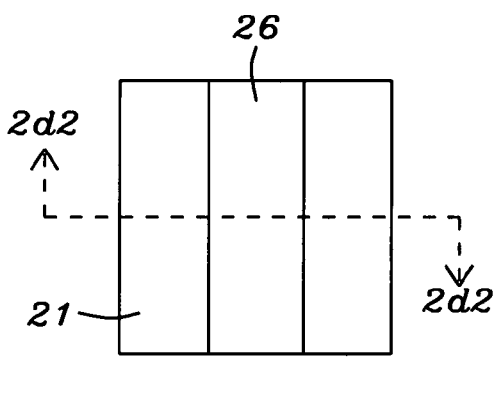
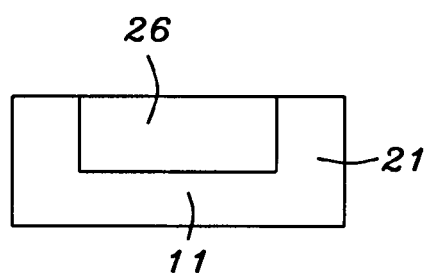
FIG. 2d1      FIG. 2d2
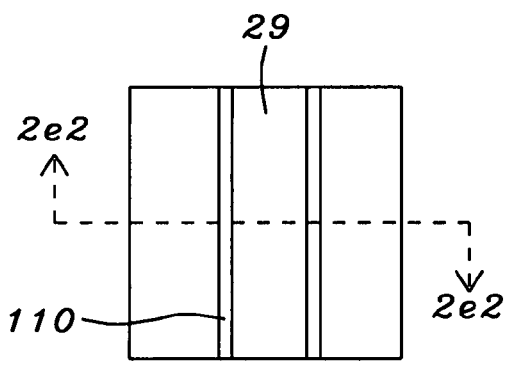
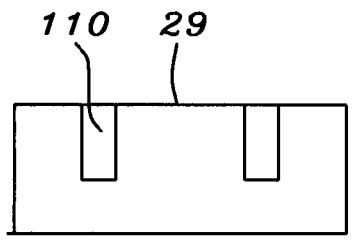
FIG. 2e1      FIG. 2e2

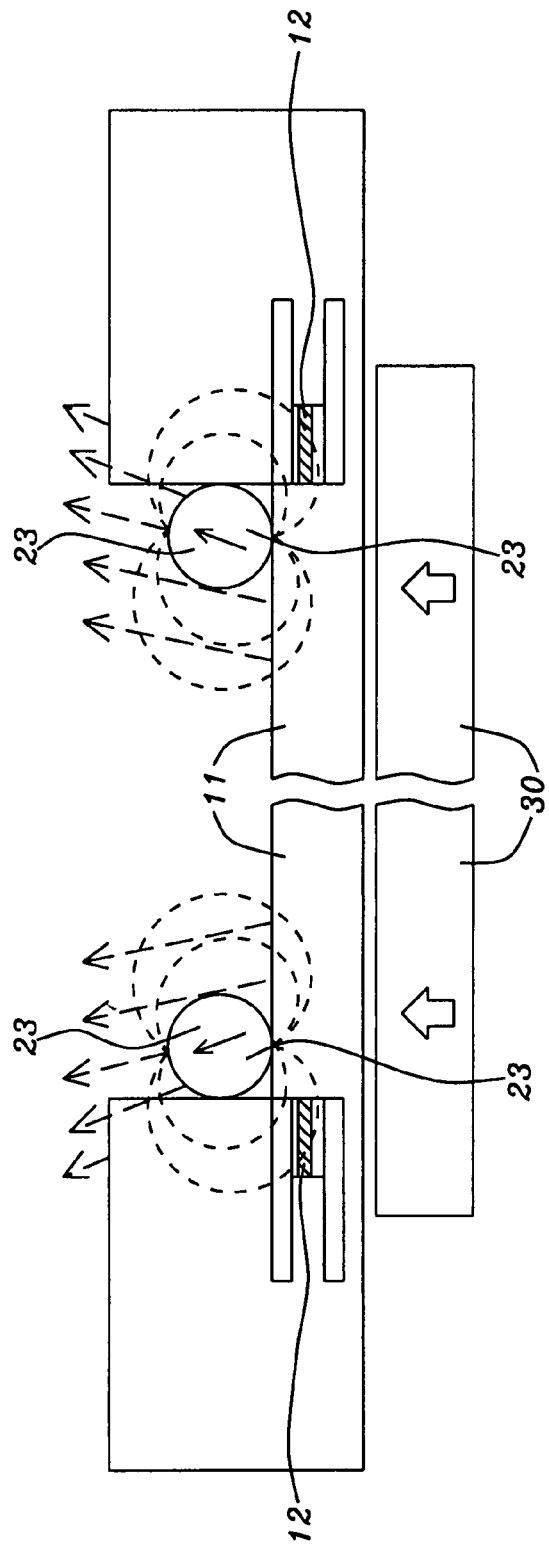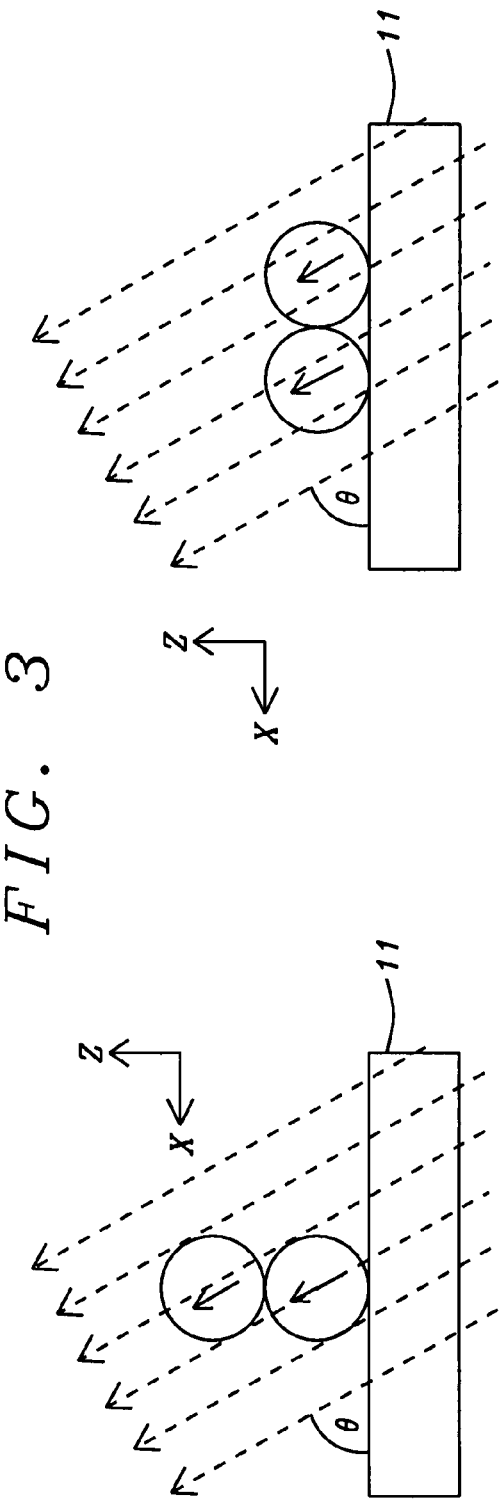

DISCRETE CONTACT MR BIO-SENSOR WITH MAGNETIC LABEL FIELD ALIGNMENT

FIELD OF THE INVENTION

The invention relates to the general field of micro-particle assays with particular reference to detection and identification of all such particles within the environment being investigated.

BACKGROUND OF THE INVENTION

It is a widely adopted sample separation method to selectively bind magnetic labels to biological cells and molecules and utilize the labels' magnetic property to separate the cells and molecules from the biological solution with an externally applied magnetic field. The selective bindings commonly used are polynucleic acid bindings or hybridizations (RNA and DNA), many types of ligand to receptor bindings, as well as antibody to antigen bindings.

With the same biological binding process, it has been a primary purpose of many prior arts to detect the magnetic field emanating from the bound magnetic labels with magneto-resistive (MR) sensors. Thus, the detection and counting of the cells and molecules can be accomplished without using extra step of dye-staining, complex optical imaging components and expensive cytometry systems. In the form of a binding assay, such magnetic detection is expected to achieve single molecule and single cell accuracy. Meanwhile, it has much less complexity and lower cost. Because of the MR sensor is entirely solid state, such magnetic based detection/counting device also shows the promise of small-form-factor hand held capability that enables fast, efficient and economically viable biological and medical applications, such as early detection of cancer and in-field virus or bacteria monitoring.

For molecule detection, binding assay to detect target molecules is already a widely used technique in biological, biochemical and medical areas. The target molecules in these bindings, for example, proteins, RNA and DNA, can also be a distinctive component or product of viruses, bacteria and cells, which may be the actual objects of interest for the detection. In a binding assay, the binding molecules are attached to a solid substrate as "capture molecules". When the assay is exposed to a liquid-form sample, where the target molecules attached to a physical label are contained, the binding molecules capture the target molecules with the specific-bindings and immobilize the target molecules on the surface. This capture process is also called "recognition". In various previous techniques utilizing the labeled binding process, the labels originally attached to the target molecule are also immobilized on the surface after the recognition process. The labels are either bound together with the target molecules on the surface ("sandwich" assay) or by themselves ("competitive" assay). After removal of the non-specific-binding labels, the bound labels can then be made to generate measurable signals to indicate presence and even population of the target molecules.

For cell detection, specific binding processes usually exist between the biologically coated magnetic labels and the cells, where antibody-antigen binding between the labels and the cells are used. The biological cells can be normal blood cells, body cells, cancer cells and other malignant cells. Cell sizes usually vary from micron size to tens of microns. The antigen binding sites on cells usually vary from thousands to hundreds of thousands number. Magnetic labels as small as submicron particles can also be used to form full coverage of the cell surface. Therefore, each cell can be regarded as a single detectable entity. Quantization of different cells not only can serve simple purposes, for example like a normal blood test, but also as a measure of existence of various diseases.

Using MR sensor to detect the magnetic field from the magnetic labels is regarded the most promising method to achieve the goal of on-chip and hand-held molecule and cell counting devices. In prior arts, the MR devices are embedded underneath the binding surface and covered by a protection layer. When the magnetic labels are bound to the surface on the top of a MR sensor, they can generate a magnetic field spontaneously, or, for super-paramagnetic labels, in the presence of an applied magnetic field. This magnetic field from the magnetic labels can then change the MR sensor's resistance state. With a sense current passing through the sensor, a measurable voltage signal can be produced.

The magnetic labels used in previous studies [1-10] or patents [11-13] are usually super-paramagnetic labels or nano-particles that have no magnetic moment at room temperature in the absence of an externally applied magnetic field. Such labels are desired for biological applications because they do not aggregate under zero field conditions. The labels or particles used in these prior arts usually range in size from tens of nanometers to several microns. When the labels attach to a surface after the recognition process, there can be multiple labels attached to a single MR device, one label per device, or one label on multiple devices. However, the sensing mechanism is generally the same. When the magnetic labels are attached to the MR sensor top surface, the field generated by the magnetic moment of the label will either act directly on the MR sensor below it or it can cancel out a portion of the external magnetic field that is acting on the sensor.

FIG. 1 schematically illustrates the basic setup and methodology described above. Magnetic label 10 is attached to the MR sensor surface through the binding pairs 15 after the recognition process. The MR sensor is usually a giant-magneto-resistive (GMR) or a tunneling-magneto-resistive (TMR) device, which includes magnetic free layer 12, non-magnetic spacer layer 13 and magnetic reference layer 14. Spacer 13 is a conductive layer in GMR sensors and a tunneling insulator layer in TMR sensors.

Magnetization of reference layer 14, as represented by $M_{reference}$, is fixed in the X axis direction through exchange field from other underneath magnetic layers not shown in the figure. Reference layer magnetization does not change direction under normal magnetic fields. The free layer's magnetization is in the Y axis direction under zero applied field achieved by a bias field $H_{bias}$ applied in Y axis or by the shape anisotropy of thin film. With a DC current flowing across the device, either in the XY plane or perpendicularly along Z axis, the voltage across the device will change with the MR resistance change and produces a measurable voltage signal.

In prior studies and patents, several detection schemes were used. One commonly used scheme is applying a magnetic field in the transverse direction 14-10, 12-[3], i.e. along the X axis in FIG. 1. This applied field magnetizes the magnetic label along the field direction. The label's magnetic moment produces a magnetic field in the MR sensor below and partially cancels the applied magnetic field acting on the MR sensor. Therefore, under the same applied field conditions, the voltage across the sensor when a label is present differs from when there is no label attached. The presence of the label is detected with this voltage amplitude difference.

Another label sensing scheme, known as BARC [1-3,11], is to apply a DC field perpendicular to the film plane, i.e. along the Z axis direction. This DC field magnetizes the label vertically, the in-plane component of the field generated by the label moment in the MR sensor below, rotating the free layer magnetizations accordingly. If the reference layer magnetization is aligned along the Y axis, or a multi-layer MR structure is used, this rotation will produce a resistance change. It is referred to as a "scissoring mode" [11]. In both schemes, a reference MR sensor to which labels will not attach at any time is always needed as a comparison basis for the voltage change.

Known Prior Art Problems:

Random label binding sites. A key problem facing the current and prior art is that which binding sites get labeled is largely random. The detection scheme described by FIG. 1 assumes that when a label becomes bound to the surface it is directly above the MR sensor. One-on-one binding of this sort is, however, not readily achievable in practice. Almost all the prior art approaches assume that the positioning of the labels, once they have settled on the surface, will be random. The MR sensor is usually made to be similar or larger in size than the labels so as to increase the probability of labels landing on them so the number of labels ending up at any given sensor varies. Additionally, labels may quite likely land on the edge of, or even between, the sensors, This uncontrolled binding of the labels produces signal variations due to the different number of labels on each sensor.

Quantization by signal amplitude: Detection, as described in prior art, is mainly focused on producing a correlation between the number of labels on a MR sensor and the voltage output of that sensor. Given this correlation, the population of the labels can then be estimated from the observed voltage levels. However, as discussed above, the random location of the labels produces an intrinsic signal fluctuation even if the number of labels on each sensor is the same. Additionally, the label itself will always have shape, size and composition variations. Thus, the correlation is further blurred and sensing accuracy is more reduced.

Additionally, since most of the large sensors used in prior arts do not have a hard bias structure to pin the free layer magnetization, for example as in BARC, domain structures are very likely to form at the sensor edges, leading to low frequency large amplitude Barkhausen noise. With all the noise and fluctuation sources acting together, the population estimation accuracy can be severely limited and the fluctuations can become large enough to inhibit practical binding assay applications that are based on the detection of the absolute field strength.

Large sensor size: The size of the individual sensors shown in some of the prior arts is usually quite large—about several microns in size. Although such large sensors have a higher probability that magnetic labels will settle on them, their signal is also significantly reduced. When a label sits on a large sensor, only the label's in-plane field causes free layer magnetization rotation (which is localized at the sensor area right beneath the label). Such fields decrease very quickly towards the sensor's edges. Since the signal is generated by fields anywhere in the full sensor area, the signal produced by a magnetic label will decrease as the sensor size increases.

Sensor to sensor signal variation: In the conventional 2-D sensor matrix used in the prior arts, the binding site variations can be partially alleviated by a 2-D signal mapping. With a 2D mapping of the signal amplitude, the label can be located from its signal amplitude. However, such a scheme makes the assumption that each cell has nearly identical response to the magnetic label and that such response can be characterized. For the detection of multiple labels attached to the surface in clusters, the sensor size needs to be much smaller than a single label and the sensor to sensor distance needs to be very small in order to achieve enough sampling of the magnetic field from every label. However, the patterned MR sensors used for assays have intrinsic signal variations between themselves due to fabrication uncertainty. Also, due to the same uncertainty, the sensor cannot be too small or the sensor to sensor signal and response variation will be too large. Additionally, the large size of the transistors used to power each sensor individually limits the maximum sensor areal density. Therefore, a limitation on the spatially resolution of the cell matrix exists. More importantly, since the patterned MR sensors in the assays do not include a hard bias structure, the MR sensors may have large sensitivity fluctuations because of unpinned edges and leads larger sensitivity variations limits the detection accuracy.

In summary, label detection and population counting in the presence of uncontrolled binding processes and amplitude detection are regarded as impediments to achieving the goal of single label and single molecule detection. Detection aided by a 2D mapping of the MR signal is limited by the spatial resolution from the minimal sensor size and sensor to sensor distance. The large sensor to sensor signal variation, sensor intrinsic signal fluctuation due to fabrication and large noise from unbiased MR structures are also serious challenges in the prior art.

To overcome these problems, a method that can avoid the effects of random label distribution on the binding surface and that can eliminate signal fluctuations arising from label location differences is needed. Such a method should not rely on measurement of the absolute label field magnitude to minimize the effect of variation of the label physical size and magnetic property. Label detection with spatial resolution not limited by the sensor spacing is desired. An MR sensor with no free edges is needed for lowering noise levels. Signal sampling at higher frequencies than currently being used in prior arts is also preferred to reduce the effect of low frequency 1/f noise from the sensor as well as other electrical components within the detection system.

REFERENCES

[1] D. R. Baselt et al., "A biosensor based on magnetoresistance technology," *Biosens. Bioelectron.*, vol. 13, pp. 731-739, October 1998.

[2] R. L. Edelstein et al., "The BARC biosensor applied to the detection of biological warfare agents," *Biosens. Bioelectron.*, vol. 14, pp. 805-813, January 2000.

[3] M. M. Miller et al., "A DNA array sensor utilizing magnetic microlabels and magnetoelectronic detection," *J. Magn. Magn. Mater.*, vol. 225, pp. 138-144, April 2001.

[4] D. L. Graham, H. Ferreira, J. Bernardo, P. P. Freitas, and J. M. S. Cabral, "Single magnetic microsphere placement and detection on-chip using current line designs with integrated spin valve sensors: Biotechnological applications," *J. Appl. Phys.*, vol. 91, pp. 7786-7788, May 2002.

[5] H. Ferreira, D. L. Graham, P. P. Freitas, and J. M. S. Cabral, "Biodetection using magnetically labeled biomolecules and arrays," *J. Appl. Phys.*, vol. 93, pp. 7281, May 2003.

[6] G. Li et al., "Detection of single micron-sized magnetic label and magnetic nanoparticles using spin valve sensors for biological applications," *J. Appl. Phys.*, vol. 93, pp. 7557-7559, May 2003.

[7] G. Li, S. X. Wang and S. Sun, "Model and experiment of detecting multiple magnetic nanoparticles as biomolecular labels by spin valve sesnors," *IEEE Trans. Magn.*, vol. 40, pp. 3000, 2004

[8] S. X. Wang et al., "Towards a magnetic microarray for sensitive diagnostics," J. Magn. Magn. Mater., vol. 293, pp. 731-736, 2005.

[9] W. Shen, X. Liu, D. Mazumdar and G. Xiao, "In situ detection of single micron-sized magnetic labels using magnetic," Appl. Phys. Lett., vol. 86, pp. 253901, 2005.

[10] H. Ferreira, N. Feliciano, D. L. Graham and P. P. Freitas, "Effect of spin-valve sensor magnetostatic fields on nano-label detection," J. Appl. Phys., vol. 97, pp. 10Q904, 2005.

[11] D. R. Baselt, "Biosensor using magnetically detected label," U.S. Pat. No. 5,981,297 (1999)

[12] M. C. Tondra, "Magnetizable Label Detector," U.S. Pat. No. 6,743,639 B1 (2004)

[13] M. C. Tondra, "Magnetizable Label Detector," U.S. Pat. No. 6,875,621 B2 (2005)

[14] For example, the "Sintered Neodymium Magnets" from Eneflux Armtek Magnetics (EAM)

[15] M. Murakami, Y. Nishimura, T. Hirooka and S. Sasaki and 1. Yagi, "Interaction of multiple iron balls in magnetic fields," J. Appl. Phys., vol. 97, pp. 083911, 2005.

[16] S. Chikazumi, "Physics of Ferromagnetism,", $2^{nd}$ Edition, 1997, Oxford University Press, p.p. 603.

A routine search of the prior art was performed with the following references of interest being found:

U.S. Pat. Nos. 6,743,639 and 6,875,621 (Tondra) disclose a molecule binding layer on the side of a substrate. Individual sensors are interconnected. U.S. Pat. No. 7,179,383 (Porter et al) shows a GMR sensor detecting magnetic labels in a flowing fluid stream. U.S. Pat. No. 7,172,904 (Engel et al) describes an MRAM to detect magnetic beads.

U.S. Pat. No. 5,981,297 (Baselt) teaches a magnetic field sensor that detects the presence of magnetic particles. U.S. Patent Application 2007/0159175 (Prins) shows on-chip magnetic sensors to detect different types of magnetic particles or molecules. U.S. Patent Application 2007/0114180 (Ramanathan et al) discloses detection of biological cells and molecules.

SUMMARY OF THE INVENTION

It has been an object of at least one embodiment of the present invention to detect the presence and quantify the population of, magnetic entities with peak pattern recognition from the differential waveform to achieve a single biological entity detection Another object of at least one embodiment of the present invention has been to minimize label-to-sensor physical distance variations by use of controlled field gradient and physical confinement structure design to enhance the precision of label localization.

Still another object of at least one embodiment of the present invention has been to reduce magnetic noise by minimizing the effects of free magnetic edge charges through use of a continuous MR sensor and/or edge pinning with bias field.

A further object of at least one embodiment of the present invention has been to use a continuous MR sensor having discrete contact pads to generate a semi-continuous differential signal waveform.

A still further object of at least one embodiment of the present invention has been to relieve the requirement of large sensor size.

Yet another object of at least one embodiment of the present invention has been to enable biological cell detection by MR sensors without needing to remove unbound magnetic labels or particles An additional object of at least one embodiment of the present invention has been to achieve simultaneous counting and identification of multiple biological entities.

These objects have been achieved by using as the detector a well-shaped structure through which is directed an externally applied magnetic field. This external field is shaped so that there is a gradient over the region where the walls and floor of the well meet. This has the effect of drawing the target molecules or cells under detection up against the wall and floor. Said molecules or cells have been rendered magnetic by magnetized nano-particles (labels) that bind to the molecules or to the surface of the cells as a result of biological recognition.

Detection of the particles is achieved by embedding in the well's wall (or floor in some embodiments) an array of magnetic field detection devices (typically GMR or TMR devices) each of which may be individually interrogated. By sequentially scanning all devices in the well a wave pattern is formed with peaks showing the locations of the particles.

Interference by unattached labels, that may have fallen into the well along with the main particles, is eliminated by providing holes in the well's floor through which the labels, but not the (much larger) particles (i.e. the above referenced molecules or cells) will fall. Many variations in the shapes of the well and the applied field are possible, those that are most preferred being discussed in greater detail.

BRIEF DESCRIPTION OF THE DRAWINGS

FIG. 1 is a schematic view of a magnetic label being attached to a MR sensor surface by biological or chemical binding pairs after the recognition process FIG. 2a schematically illustrates a preferred embodiment of the invention which is a well structure comprising a non-magnetic floor and a wall made up of MR sensors whose free layers terminate at the wall's inside surface.

FIGS. 2b-2e2 illustrate some of the many variations possible of the basic well of FIG. 2a, including an annulus (2c1 and 2c2) a trench (2d1 and 2d2) and parallel trenches (2e1 and 2e2).

FIG. 3 shows, as an example, the general locations, relative to the floor and wall, of the magnetized particles, the external magnet, including the gradient field at the edges, the particles' magnetic field, and the MR sensors.

FIGS. 4a, 4b, 5a, and 5b show various possible arrangements of the magnetic particles relative to the floor and the wall, with FIGS. 4b and 5b showing the positions desired for optimum detection.

Figure 5A:
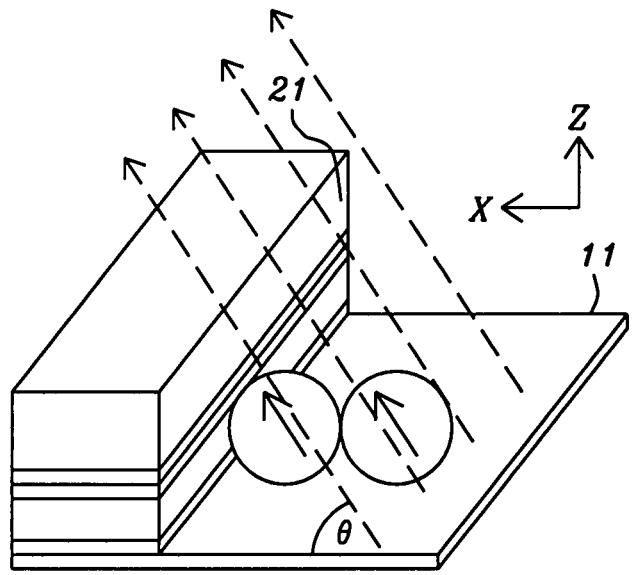

DESCRIPTION OF THE PREFERRED EMBODIMENTS a) Discrete Contact Continuous MR Sensor:

FIG. 2a shows a 3D schematic of the discrete contact MR sensor structure used for magnetic label detection by the present invention. As also shown in the plan view of FIG. 2b, the structure is a ring of TMR/GMR devices 22 embedded in non-magnetic material 21. It includes a well that is suitable for label confinement. The inner edges of the MR ring form the inside wall of the well. If needed, a protective layer can be deposited on the wall and floor of the well to avoid MR sensor corrosion.

Magnetic labels 23 suspended in the biological liquid are dropped into the well. The force of an external magnetic field, readily supplied by a permanent magnetic disk located beneath the well, pulls the labels to floor 11 and aligns them along the well edges. With a proper adjustment of the MR sensor height relative to the well's floor, the magnetic moment of the labels can generate enough in-plane field in the MR sensor to cause the sensor's free layer magnetization to rotate.

It is an important feature of the invention that this magnetization rotation is confined to those MR sensors located closest to the labels. By sequentially measuring the resistance between each pair of top and bottom contact pads along the ring circumference, a differential signal waveform can be generated, making identification of the particular sensor(s) affected by the label's presence readily achievable.

By counting signal peaks around the inner circumference of the well, the number of captured labels can be determined. Given the known correlation between the magnetic labels and the biological entities, the biological entity population can therefore be estimated, down to single molecule or single cell resolution. For the case of closely packed multiple labels, the sensed waveform can be viewed as superposition of the waveform from a single label. Signal processing techniques, for example equalization and partial-response-maximum-likelihood (PRML) channel used in data storage devices, can be easily employed to derive the number of labels from the super-positioned waveform.

More importantly, the alignment of the magnetic labels along the sensor edges can, in theory, produce zero position variation of the magnetic labels relative to the MR sensor with a specially designed alignment magnet underneath or surrounding the MR sensor. This is mainly due to the fact that the physical structure of the well can have precise depth and size control comparable to what is achieved in state-of-the-art magnetic head and MRAM fabrication processes. Field gradients from specially designed magnets can also assure non-agglomeration of magnetic labels in the magnetic field. Thus, signal fluctuations due to label number and position variations can be largely eliminated.

The invention is not limited to the cylindrical well structure shown in FIGS. 2a and 2b. As exemplified in FIGS. 2c1-2e2, other possible shapes for the well include, but are not limited to the following:

annulus 27, shown in plan view (FIG. 2c1) and cross-section (FIG. 2c2) which includes a non-magnetic island portion 25, formed within substrate 21;

trench 26, also shown in plan view (FIG. 2d1) and cross-section (FIG. 2d2); and various minor variations such as multiple concentric annuli or multiple trenches side by side (see FIGS. 2e1 and 2e2). For the invention to operate as claimed it is not essential that any of the shapes used to form the well follow precise geometric form a. i.e. they need not be symmetrical, perfectly straight and/or parallel, etc.

b) Schemes for MR Sensor and Gradient Control:

The labels can be magnetized either longitudinally in plane or perpendicularly but it is the in-plane field from the label magnetic moment that always causes the MR sensor's free layer magnetization to rotate. Therefore, the sensor positioning relative to the magnetic labels needs to maximize the in-plane magnetic flux that goes through the sensor to produce high signal.

FIG. 3 shows one way to apply the field and position the sensor. Here the magnetizing field is provided by a thin cylindrical permanent magnet 30 beneath the sensor, whose magnetization is perpendicular to the sensor plane. The sensor and well structure is assumed to be circular as shown in FIG. 2a. but fields shaped to match the outlines of other well shapes could also be used where appropriate. The magnetic field from the magnet underneath is essentially perpendicular until it reaches the edges of the magnet. Thus magnetic particles 23 on the surface of floor 11 of the well are also magnetized, mostly vertically. Additionally, due to the thin disk shape of the magnet, the field that it produces is weakest at its center and strongest at its edges. Therefore, there is a field gradient directed towards the magnet's edges, as indicated by the higher density of the field lines at the magnet edges in FIG. 3.

This gradient pulls the magnetic labels up against the inside wall of the confining well. By aligning the center lines of the magnet and the well, the field gradient and magnitude will be close to uniform along the well edge. Thus, the magnetic labels will tend to be uniformly distributed around the inside wall of the MR sensor. The in-plane component of the field from the aligned labels then causes free layer magnetization to rotate locally to produce a resistance change. In FIG. 3 the MR sensor ring is located at a lower level than the label so as to capture the in-plane label magnetic flux.

FIG. 4a illustrates what is required for the labels to form a single layer on floor 11 rather than stacking up on top of one other. Thus the horizontal configuration of FIG. 4b must require less energy to form than the vertical configuration of FIG. 4A. For this to be the case, the field gradient along vertical direction needs to satisfy $$\frac{dH_a}{dz} \geq \frac{\pi M(H_a)}{4R}(\sin^2\theta - \cos^2\theta) \tag{1}$$

where R is the label's radius, $H_a$ the applied field strength, $\theta$ the angle of the applied field, relative to the floor, and $M(H_a)$ the effective label magnetization under the applied field Z. Therefore, for field angle less than 45°, the labels will automatically align on the floor surface. Although Eq. (1) also shows that, for perpendicular field where $\theta=90°$, a relatively high gradient will be needed to achieve non-stacking situation, for the field scheme as shown in FIG. 4, a tilted magnetizing field exists at the inner edge of the well and helps field gradient to satisfy the Eq (1) condition.

Figure 5B:
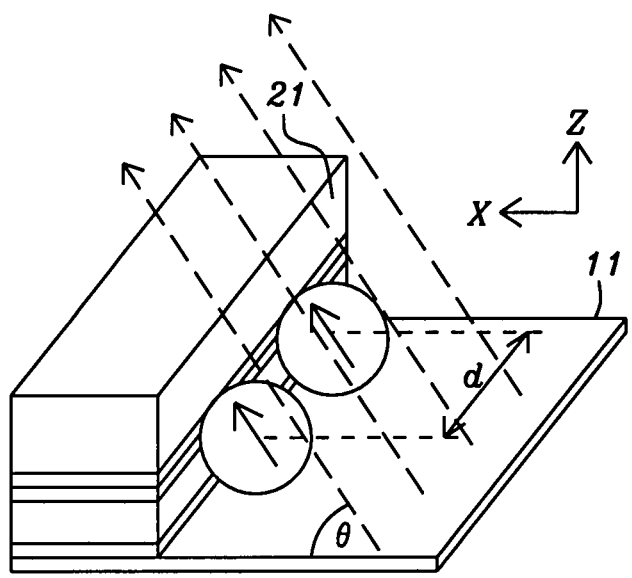

For the case of particles not forming in-plane chains on the floor surface 11, but always being aligned along the wall edge, similar analysis as in FIG. 4a applies. Assuming the distance between the two labels is d after the alignment, the minimum field gradient needed for the FIG. 5b configuration to have a lower energy of formation than the FIG. 5a configuration is shown in eqn. 2:

$$\frac{dH_a}{dx} \geq \frac{\pi M(H_a)}{12R}\left(2\cos^2\theta - \sin^2\theta + \frac{8R^3}{d^3}\right) \quad (2)$$

For popular magnetic bio-labeling, the magnetization at moderate applied fields is usually small. For example, for Dynal Label M-280 it has been shown [1] that at 1 kOe (80 kA/m) magnetizing field, the label magnetization is around 10 emu/cc (10 kA/m). Assuming a label size of 10 μm, for $\theta=90°$, a vertical field gradient of 1.6 kOe/mm (and a zero x direction gradient) is able to satisfy both conditions in Eq. (1) and (2).

For $\theta=45°$, a zero vertical field gradient and an x direction gradient of 800 Oe/mm is able to satisfy both conditions. Such field gradients are easy to provide if a cylindrical magnet as in FIG. 3 is used. For example, a thin NdFeB permanent magnetic with a thickness in the millimeter range and the distance between the well floor 11 and the top surface of the magnet being less than 1 mm, will usually satisfy both conditions in Eqns. (1) and (2).

When the labels are magnetized and pulled outwards to the floor's edge, as shown in FIG. 3, the magnetic interaction between the labels is always repulsive. This helps to maintain a certain amount of separation between labels. The larger the label moment the larger the separation between labels. This mutual repulsion between magnetic spheres that keep them separated when in a magnetized state is well documented in prior art literature regarding magnetic levitation [15].

In addition to the MR sensor placement and field application scheme shown in FIG. 3, there are several other possible schemes, a few of which (but by no means all) are illustrated in FIG. 6a-6f. The operative idea is for an externally applied magnetic field to attract the labels to the well's edge, aligning them with a sufficient gradient to form a single layer/row along the edge. Additionally, the continuous MR stack needs to be positioned so as to be able to sense the maximum label field.

Figure 6A:
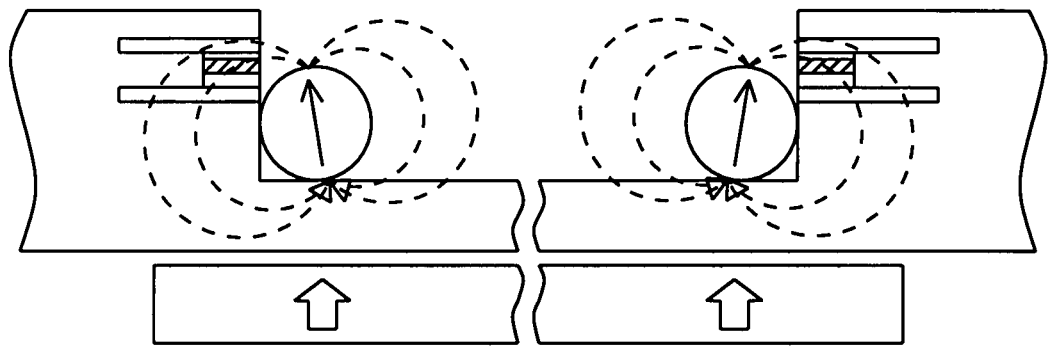
FIGS. 6a-6f show a selection of some of the possible configurations for the invention, particularly the shape and location of the external magnet, the location of the MR sensor, and the magnetization of the particles being detected.

FIG. 6a illustrates the same label and field application scheme seen in FIG. 3. However, the sensor stack has been elevated to sense the in-plane flux of the magnetic labels originating at the top of the label. This sensor and well structure is generally easier to fabricate since the sensor inside edge can be defined together with the well's edge in a single etching step.

Figure 6B:
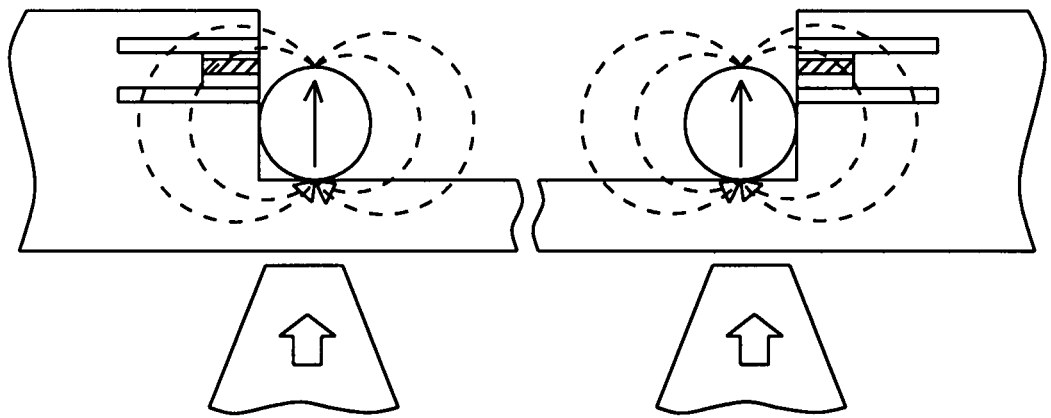

FIG. 6b also shows a similar structure as FIG. 3 but with a different field application scheme. Here the magnetic flux is locally concentrated at the well edge, enabling the field gradient to be greatly enhanced. The dashed lines represent two possible vertical locations for the MR stacks.

Figure 6C:
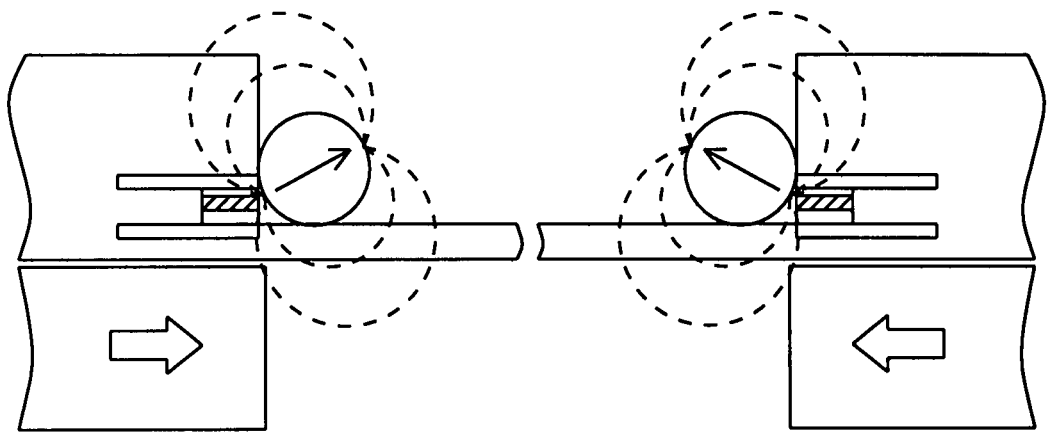
Figure 6D:
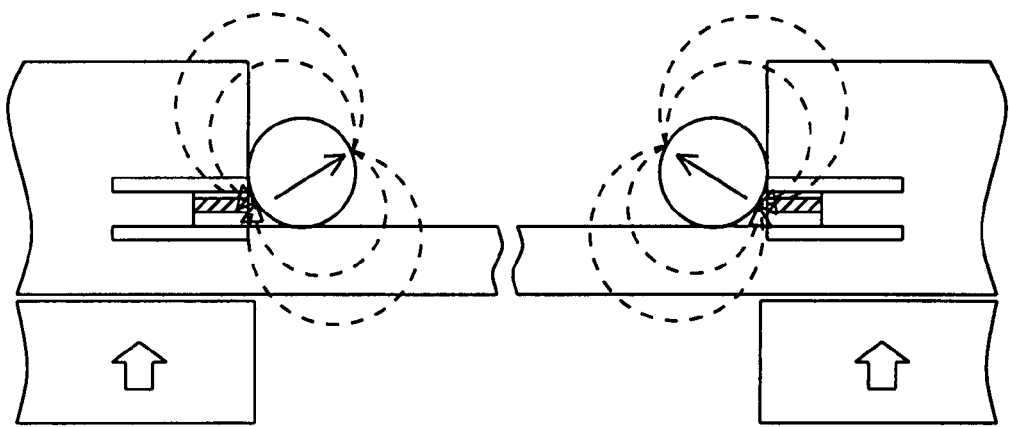

FIGS. 6c and 6d show structures wherein the labels are magnetized at an angle. The underneath magnet has a clearance that is concentric with the well center. The magnetic field from the inner edge of the magnets attracts the labels to the well edge and aligns them in the same way as discussed in FIG. 3. The difference is only the magnet's magnetization direction. The MR sensor stack's vertical position can be adjusted to sense the maximum field from the magnetized labels.

Figure 6E:
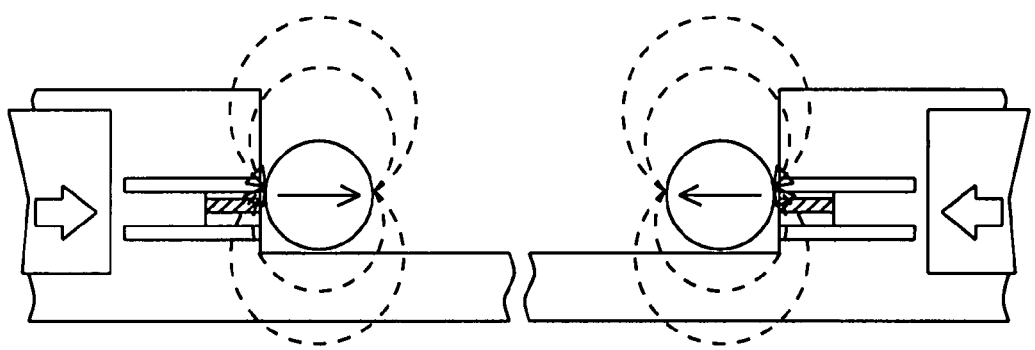
Figure 6F:
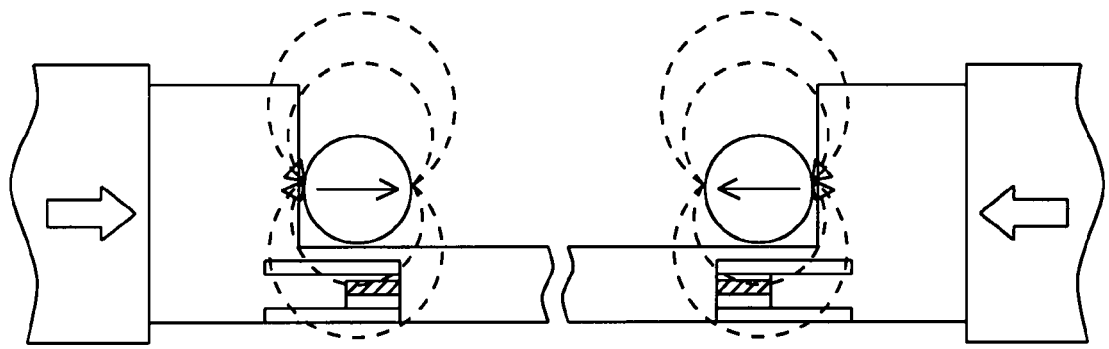

FIGS. 6e and 6f are the structures where labels are magnetized in-plane. In FIG. 6E, the MR sensor stack is located at the same height as the poles of the label and senses the magnetic field of the labels where the flux density is at its greatest. Such structures expose the MR sensor to the largest field put out by the labels.

FIG. 6f shows the case where the MR sensor is embedded below the floor's top surface and the MR labels are directly above the MR stack. When the field is applied, the label field cancels the applied field at the MR sensor. This scheme can be used to increase the signal of the MR sensor and help avoid twisted domains that may exist in the FIG. 6E structure when label permeability is relative large.

c) Cell Detection

Figure 7A:
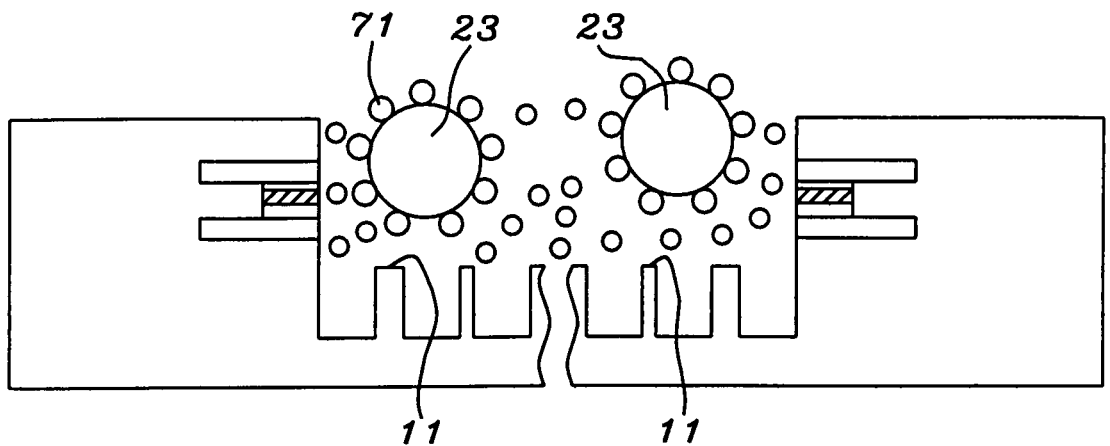
FIGS. 7a and 7b illustrate the structure used by the invention to separate magnetic particles that are to be detected from unattached, much smaller, magnetic labels that may have fallen into the same well.

FIG. 7 shows one possible, but not unique, method for detecting cells using the discrete contact continuous MR sensor. FIG. 7a shows how cells coated with magnetic labels may enter the well at the same time as unbound magnetic labels. The magnetic particles could have been coated in a prior step before the solution was injected into the well. Alternatively, the coating process can also be realized inside the well with the magnetic field being turned off.

Figure 7B:
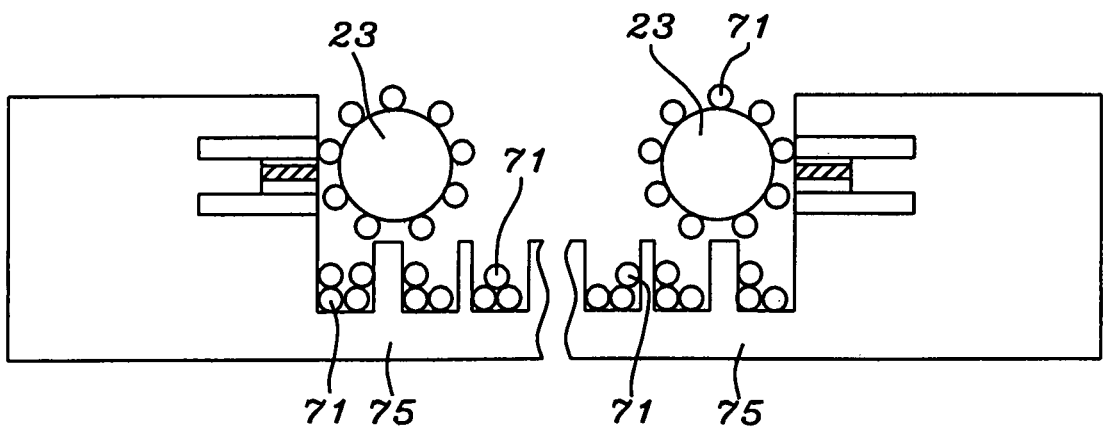

To keep unbound labels away from the MR sensors microholes (or micro-slots) are formed in the well's floor. As seen in FIG. 7b, these holes/slots are large enough to allow the magnetic particles/labels to pass but small enough to ensure that cells will remain above the well floor. When the field is applied, the cells will be attracted to the well's edge in the same way as isolated magnetic labels. However, because of the holes and slots, unbound magnetic labels will fall through the floor and only the much larger cells will remain and align to the well's edge. With proper positioning of the MR sensor, the fields originating at the unbound labels field will not affect the MR sensor so only cells will produce a signal in the MR sensor. This cell detection scheme does require the cell size to be much larger than the label size. For example, a CD4-T cell is about 10 μm in diameter while a typical label size is preferably in the range of tens to hundreds of nanometer. This will allow the hole/slot size to be of the order of a micron making successful removal of unbound labels can practical.

For cell detection, the cell size is usually quite large. However, since only a single layer of labels gets coated on the surface of the cell, the magnetic properties of a coated cell will be similar to those of a spherical magnetic shell. The magnetic field from such a shell structure is much smaller than from a solid magnet of the same shape and size. Thus, a high sensitivity configuration such as the one illustrated in FIG. 6e, where the MR sensor is located at the flux concentration point of the label, is our preferred structure for detecting coated cells.

Specific Embodiments

Embodiment 1A—The MR sensor is a current-perpendicular-to-plane (CPP) device where the current direction during MR operation is perpendicular to the sensor film plane. As schematically illustrated in FIG. 1, free layer 12, spacer 13 (tunnel barrier for TMR and conductive for GMR), and reference layer 14 form a continuous closed loop or are continuous in segments. Isolated electrical contact leads exist on top and bottom of the MR sensor and form a linear array. Each of the above layers can themselves be multi-layer films. During read-back, the signal is retrieved by sensing the voltage/resistance/current values between one pair, or multiple pairs, of top and bottom contact pads.

Embodiment 1B—The MR sensor is a current-in-plane (CIP) where the current direction during MR operation is within the film plane.

Confinement Structure

Embodiment 2A—A closure well, which can be in the shape of, circular, ellipsoid, triangle, rectangle, square, pentagon, hexagon, is created within a substrate 21 (see FIG. 2. The liquid form sample resides within the well space. With an applied field gradient, the magnetic labels, or cells coated with magnetic labels, will be aligned along the inner edge, sitting on the bottom surface. The well edge 7 is optionally perpendicular to bottom surface 8.

Embodiment 2B—Every other aspect is the same as Embodiment 2A except that another solid structure 25 (see FIG. 2) exists within the well. This solid structure is optionally of the same material as substrate 21. Structure 25 has same shape as the well. The liquid form sample resides within the depression. In the presence of an applied field gradient, the magnetic labels or cells coated with magnetic labels will be aligned along the well walls while sitting on floor surface 11. The bottom width of the trench is preferred to be larger than the size of a single label/cell, but smaller than twice the size of a single label/cell. The wall is optionally perpendicular to the floor.

Embodiment 2C—A trench 26 is formed within a substrate 21 (see FIG. 2d). The liquid sample resides within the trench. In an applied field gradient, the magnetic labels or cells coated with magnetic labels will be aligned along the inside wall, sitting on the bottom surface. The trench's edge is optionally perpendicular to the floor. The trench's shape along the length direction is optionally straight over its entire length. The two edges along the trench length direction are optionally parallel for the entire length.

Embodiment 2D—Every other aspect is the same as Embodiment 2C except that another solid structure 29 exists within the trench. This solid structure is optionally of the same material as the substrate 21. Structure 29 has the same shape as the trench, its outside edges serving as inside walls for the two trenches. The liquid sample resides within the trenches. With applied field gradient, the magnetic labels or cells coated with magnetic labels will be aligned along the inside walls, sitting on the floor. The bottom width of the trench should be made larger than the size of a single label/cell but smaller than twice the size of a single label/cell. The structure's walls are optionally perpendicular to floor 11.

Figure 8A:
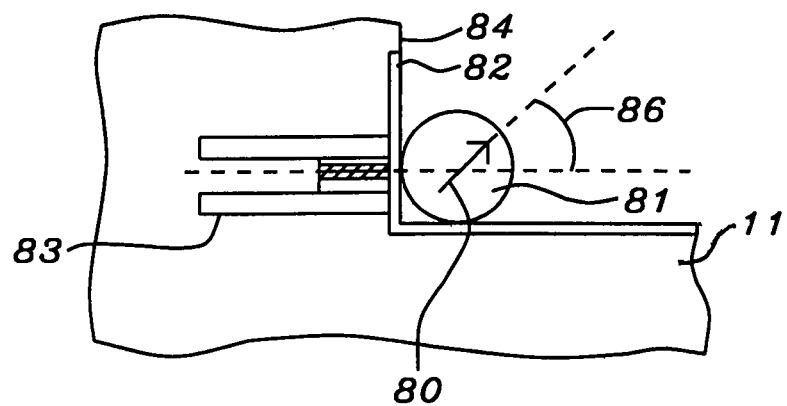
FIGS. 8a and 8b illustrate embodiments 3A-3C which teach two basic placement schemes for the MR detector.

Embodiment 3A—The entity 23 coated with magnetic labels, is aligned by the externally applied magnetic field gradient against the wall and floor. As seen in FIG. 8a, the externally applied magnetic field also induces a magnetization of the magnetic labels along the field direction as represented by arrow 80, which makes angle 86 relative to the horizontal plane determined by the field direction. The MR sensor 83 is located just inside wall 84. The vertical position of MR sensor 83 is any location between floor 11 and twice the height of the magnetic particle 81 that is to be detected. The magnetic field from the magnetic label will cause the free layer of the closest MR sensor to rotate at a different angle from that of an MR sensor further away from 81. If the applied field has an in-plane component that exerts a measurable effect in the MR sensor 83, the field from the magnetic label can either assist or cancel the applied field in the MR sensor, depending on the applied field direction. Otherwise, the label magnetic field acts on MR sensor 83 alone. Between the MR sensor 83 and the magnetic label (or biological entity) 81 exists an intermediate layer 82, which can comprise a protection layer and/or an over-coated biological layer. The protection layer within 82 can be a single composition layer or a multi-layer to protect the MR sensor 83 against corrosion and damage within the environment of the biological solution. The biological layer within 82 can capture and bind the target molecules or cells to the surface.

Figure 8B:
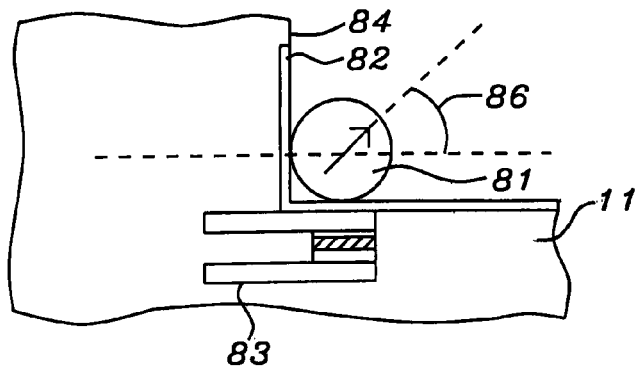

Embodiment 3B—Every other aspect is the same as Embodiment 3A except that the vertical position of the MR sensor 83 is such that its sensing layer or free layer is below floor 11 (see FIG. 8b). Additionally, the MR sensor 83 may or may not be directly beneath the magnetic label or biological entity 81. However, minimal proximity of MR sensor 83 to entity 81 is preferred for strongest signal and best spatial resolution.

Coating and Capping

Figure 9A:
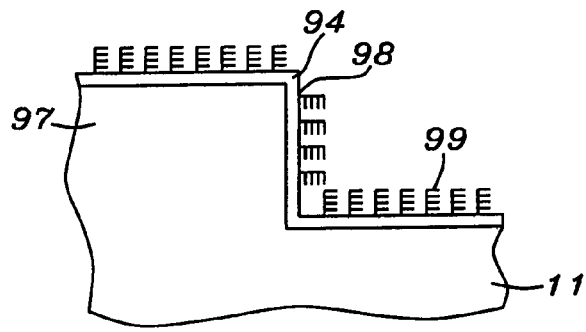
FIGS. 9a-9c illustrate embodiments 4A-4C which disclose a biological captive layer on the entire structure and methods to avoid binding outside the test area by using add-on cappings. The latter also facilitate containment of larger volumes of liquid solution in 4b and form a capillary channel with floor in 4c.

Embodiment 4A—As illustrated in FIG. 9a, for confinement structures such as in Embodiments 2, the wall 94 connects floor 11 to top surface 97. Protection layer 98 lies on the surfaces of 11, 94, and, optionally, on 97. On layer 98, there is optionally another biological layer 99, which serves the purpose of selective binding the target molecules, cells, or other biological entities on the surfaces. Layers 98 and 99 may be coated over the entire confinement structure.

Figure 9B:
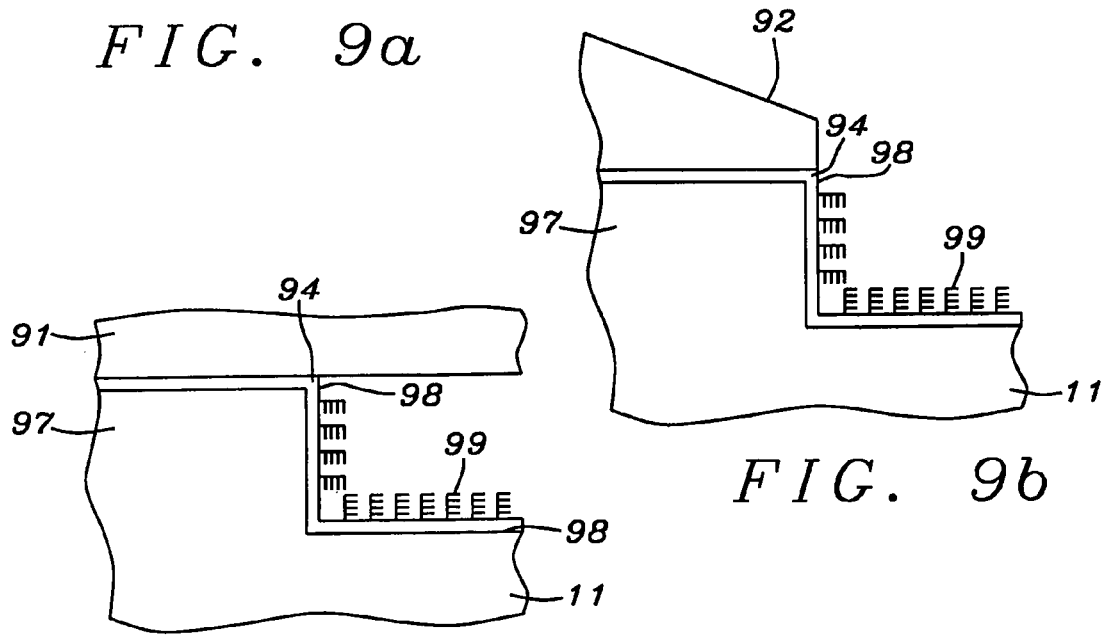

Embodiment 4B—This is the same as Embodiment 4A except that, as illustrated in FIG. 9b, there is a capping structure 92 over surface 97 and layer 98. Cap 92 has a slope and is fixed in place. The slope of 20 serves to confine the liquid sample within the test area.

Optionally, layer 99 may be above surface 97 before structure 92 is added on top. As in Embodiment 2, edge 98 connects bottom surface 11 and top surface 97. Protection layer 98 is on surfaces 11, 94 and, optionally, 97. On top of layer 98, there is, optionally, another biological layer 99, which serves the purpose of selectively binding the target molecules, cell or other biological entities on the surfaces. Layers 98 and 99 can be coated over the entire confinement structure.

Figure 9C:
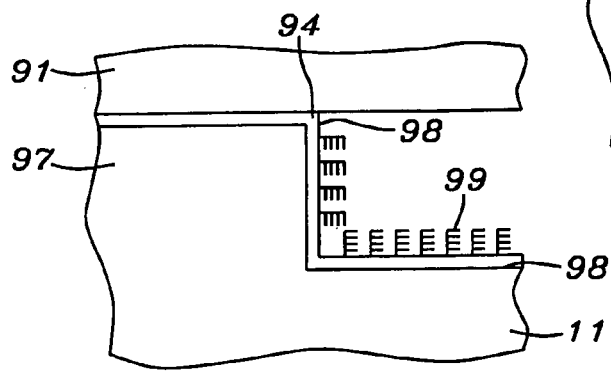

FIG. 9c shows optional cover structure 91 that is physically fixed on top of surface 97 and layer 98, forming a closure space together with edges 94 and floor 11. This closure helps to confine liquid samples within the test space. Optionally, layer 99 may be deposited over surface 97 before structure 91 is added.

(1) Sample Injection

Embodiment 5—The liquid sample can be dripped directly into the testing structure or it can be made to flow into testing structure by exerting pressure or by capillary force of conducting paths. The magnetic labels or magnetic label coated biological entities are attracted into the testing confinement by the applied magnetic field with or without a funneling structure 20 as in Embodiments 4A4C.

(2) Sample Preparation

Embodiment 6—The sample is a liquid containing magnetic label coated biological entities. Free labels may also be present in the sample.

(3) Field Application

Embodiment 7A—The magnetic field that magnetizes the magnetic labels is generated by permanent magnets. A gradient near the edge of the field serves to line up the magnetic labels (or biological entities coated with magnetic labels) against the floor and the wall. Said gradient is determined by the shape of the permanent magnets. An example (not limiting) is a thin cylinder shaped permanent magnet whose magnetization is perpendicular to the cylinder's flat surface. There is optionally a soft magnetic structure on top of the permanent magnet structure to assist magnetic field and gradient generation. Additional options are to taper the magnet shape in order to enhance the gradient and to include an embedded soft magnetic material structure within the substrate. The embedded structure can be magnetized by the permanent magnet's field.

Embodiment 7B—Every other aspect is the same as Embodiment 7A except that the magnets are electromagnets composed of conductive windings, optionally including a core of soft magnetic material.

(4) Unbound Label Treatment

Embodiment 8A—Referring once again to FIGS. 7a and 7b, magnetic labels 71 are bound to biological entities 23 that are larger in size than the magnetic labels 71. There is a pre-patterned physical well or trench structure having a floor 75, below main floor 11. The size of the well or trench structure is larger than the size of the magnetic labels but is smaller than the size of the biological entities. The sample that is added to the testing area contains label coated biological entities. Unbound magnetic labels may or may not be present at the same time. With the applied field gradient, the biological entities 23 are aligned against the wall and on top the main floor. The biological entities or the magnetic labels may optionally selectively bind to capture molecules that can be pre-coated onto the floor or wall. Due to their smaller size, any unattached magnetic labels fall into the well or trench structure of the main floor because of the same field gradient that attracts entities 23 towards floor 11 and the wall.

Embodiment 8B—The liquid sample added to the test area contains both magnetic labels attached to target molecules and magnetic labels unattached to target molecules. A first magnetic field gradient aligns all the magnetic labels along the wall and on the floor 11. The magnetic labels 71 that are attached to target molecules 23 are bound to the floor and the wall after the recognition process. With application of a second magnetic field gradient and with or without a decrease of the first field gradient strength, the magnetic labels not bound to the wall or floor are attracted to another location on the floor away from the wall.

ADVANTAGES OVER THE PRIOR ART

The present invention's use of a discrete contact continuous MR sensor for cell and molecule counting offers several advantages over the prior art:

1. The method has minimal sensor to sensor variation in sensitivity, signal level and magnetic response. Since the sensor is composed of continuous magnetic film and each sensing unit is defined by a pair of non-magnetic contact pads, large sensor to sensor signal and magnetic response variation as shown in patterned sensors in prior arts can be avoided. The sensing units used in this new method are magnetically and electrically equivalent in producing signal.
2. The method has the highest possible spatial resolution (down to a single cell or macro-molecule). Sensors used in the prior art are patterned into small islands. Due to significant sensor to sensor performance variation as pattern size is reduced, there is a lower limit to the smallest useful size that can be made. Additionally, the physical spacing between the sensors is relatively large and usually has the minimal spacing limited by electrical layer. In the present invention, the sensing unit is defined by non-signal-producing contact pads, whose spacing can be much smaller than the sensor to sensor spacing in prior art devices. The spacing can also be reduced without limitations imposed by the electrical layer which enhances the spatial resolution even further.
3. The spatial resolution may be further enhanced by an applied field, as discussed above. With proper field application and MR sensing structure design the spatial resolution can be significantly enhanced by the magnetic film's intrinsic exchange effect at higher applied field conditions.
4. Smallest limitation on label size. Because of the new method's high spatial resolution, it has minimal requirement for the smallest label size testable.
5. Differential signal. The invention does not rely on signal level detection but rather on signal peak pattern recognition that can be processed using mature signal processing techniques, for example equalization and digital PRML channels to further enhance the accuracy and SNR.
6. Much less magnetic noise and signal instability. Without patterning the free layer of the MR sensor, this method avoids the serious problem of large 1/f type magnetic noise due to sensor edge domain switching that produces low frequency signal spikes. It also reduces the magnetic noise level that is always present in small size magnetic sensors, this noise being especially high in unpinned free layer structures used in the prior art.
7. No signal average effect. In prior arts where large size sensors are being used, the signal produced by a single sensor is the result of averaging the magnetic response from the entire sensor region. It includes the region of the sensor that sees the highest label field and the region that sees the lowest field. However, the noise contributed by every region of the sensor is not reduced in amplitude by averaging. Thus, the SNR from the entire sensor is always degraded by the averaging effect. In the present invention, the MR sensor can be positioned to sense the maximum label field. Additionally, the width of the MR sensor can be reduced to within the exchange length of the free layer material, so that there is no average effect across the width direction. On the other hand, since each contact pad can also be limited to 100 nm~200 nm in size, the average effect along the sensor length direction is also minimized. Therefore, the SNR from the new method is much higher than in prior art devices, for the same label field.
8. Less signal variation caused by label position. Alignment of the magnetic labels or label-coated cells along the physical confinement edges by the external field gradient ensures that the label/cell positions relative to the MR sensor vary only slightly. Compared to the patterned sensor assay method of the prior art, the present invention is free of signal differences caused by variability of label location at the sensor edge or at the sensor center.
9. Enabling simultaneous counting of labels/cells of multiple sizes. The invention makes possible simultaneous counting of different size labels/cells within the same testing structure. This task is realized by using multiple sensors placed at different positions, including different elevations, selected so that each MR device is located where it has the greatest sensitivity detecting one particular size label/cell. By interleaving the signals from all the MR sensors, the population of different size labels is derived. If the sizes of the various labels/cells that are being counted can also be used to identify what they are, the method makes it possible to obtain a quantitative analysis of the contents of a biological solution in a single pass.

What is claimed is:
1. A method to detect magnetic particles, comprising;
providing a detector having the shape of a well, including a horizontal floor and a vertical wall that further comprises a plurality of magneto-resistive (MR) devices each having a free layer that terminates at said wall's interior surface at a fixed distance from said floor;
positioning a magnet near the well thereby providing a magnetic field that passes through the well;
inserting in said detector a liquid, within which said magnetic particles are suspended, whereby said magnetic field induces a magnetic moment in said magnetic particle, pulling said magnetic particles into the well, onto said floor, and up against said interior wall surface; and
selecting said distance of the free layer above the floor so that each particle's magnetic moment can generate enough in-plane field to cause at least one of said free layer magnetizations to rotate and thereby signal that a magnetic particle is present.
2. The method recited in claim 1 wherein said magnetic particle is a non-magnetic particle onto whose surface one or more magnetic labels have been bound.

3. The method of claim 1 further comprising sequentially measuring electrical resistance for each of said MR devices in said wall thereby generating a differential signal waveform and then, through analysis of said waveform, identifying and locating any magnetic particles inside said well.

4. The method of claim 3 further comprising counting all signal peaks in said waveform and, from a previously determined correlation between said magnetic particles and biological entities present within said detector, estimating a population value for said biological entities at a resolution level of a single biological entity.

5. The method recited in claim 1 wherein said magnet provides a uniform parallel magnetic field directed upward through, and normal to, said floor and wherein said fixed distance of said free layer above the floor is within 200% of said magnetic particle's diameter.

6. The method recited in claim 1 wherein said magnet provides a non-uniform magnetic field directed upward through, and normal to, said floor, said field being strongest beneath said wall's inside surface and wherein said free layer is located at a distance from said floor that is within 200% of said magnetic particle diameter.

7. The method recited in claim 6 further comprising making said non-uniform parallel magnetic field weakest at its center and strongest at its edges, thereby creating a field gradient directed towards the magnet's edges, said gradient serving to pull magnetic particles up against the inside wall of the confining well.

8. The method recited in claim 6 further comprising forcing said magnetic particles to form a single layer on said floor by ensuring that said non-uniform magnetic field has a gradient whose value, MG, satisfies an equation of form $$MG = \frac{dH_a}{dz} \geq \frac{\pi M(H_a)}{4R}(\sin^2\theta - \cos^2\theta)$$

where R=particle radius, $H_a$=applied field strength, $\theta$=angle of applied field relative to said floor, and $M(H_a)$=effective particle magnetization in said applied field.

9. The method recited in claim 1 wherein said magnet is located below said floor and which provides a uniform magnetic field directed to be parallel to said floor, said free layer being located at a distance from said floor that is within 400% of said particle radius R.

10. The method recited in claim 1 wherein said magnet provides a cylindrical magnetic field directed upward through, and within, said wall and wherein said free layer is located at a distance from said floor that is within 400% of said particle radius R.

11. The method recited in claim 1 wherein said magnet surrounds said wall above the floor, providing a magnetic field that is mainly parallel to said floor and wherein said free layer is located above said floor at a distance above said floor that is within 50% of one half of said magnetic particle diameter.

12. The method recited in claim 1 further comprising providing openings in said floor that are large enough to permit passage of unattached magnetic labels and small enough to block passage of said magnetic particles.

13. The method recited in claim 1 wherein said MR devices are selected from the group consisting of giant magneto-resistance (GMR) and tunneling magneto-resistance (GMR) devices.

14. The method recited in claim 1 wherein said wall has a height above said floor that exceeds twice said particle size and that also exceeds 10 microns.

15. The method recited in claim 1 wherein said wall has said wall has an inside diameter of between about 0.1 and 10 mm.

16. The method recited in claim 1 wherein said magnet is an electromagnet having a core selected from one or more members of the group consisting of Co, Fe, Pt, Pd, Nd, Sm, B, Ni, and Al.

17. A method to detect a magnetic particle having a diameter, comprising:

providing a plurality of magneto-resistive (MR) devices each of which includes a free layer;

by abutting all of said MR devices to one another, arranging said plurality of MR devices to form a ring around a center point;

contacting each of said MR devices through at least one electrically isolated electrode;

extending said floor layer inwards from all of said MR devices as far as said center point;

fabricating a wall of non-magnetic material that extends upwards from said ring, thereby, together with said floor, forming a well;

surrounding said wall and floor with a permanent magnet that provides a magnetic field parallel to said floor; and locating said free layer below said floor and extending said free layer towards said center point for a distance that is less than or equal to said magnetic particle diameter.

* * * * *